United States Patent
Robinson

(10) Patent No.: US 10,295,665 B2
(45) Date of Patent: May 21, 2019

(54) CONFIGURABLE MICROBEAMFORMER CIRCUIT FOR AN ULTRASONIC DIAGNOSTIC IMAGING SYSTEM

(75) Inventor: Andrew L. Robinson, Bellevue, WA (US)

(73) Assignee: Koninklijke Philips, N.V., Eindhoven (NL)

(*) Notice: Subject to any disclaimer, the term of this patent is extended or adjusted under 35 U.S.C. 154(b) by 1060 days.

(21) Appl. No.: 13/126,466

(22) PCT Filed: Oct. 27, 2009

(86) PCT No.: PCT/IB2009/054754
§ 371 (c)(1),
(2), (4) Date: Apr. 28, 2011

(87) PCT Pub. No.: WO2010/055428
PCT Pub. Date: May 20, 2010

(65) Prior Publication Data
US 2011/0213251 A1    Sep. 1, 2011

Related U.S. Application Data

(60) Provisional application No. 61/113,258, filed on Nov. 11, 2008.

(51) Int. Cl.
*A61B 8/00* (2006.01)
*G01S 15/89* (2006.01)
(Continued)

(52) U.S. Cl.
CPC ........ *G01S 15/8909* (2013.01); *A61B 8/4483* (2013.01); *G01S 7/5208* (2013.01);
(Continued)

(58) Field of Classification Search
CPC .... G10K 11/345; A61B 8/4483; A61B 8/4494
See application file for complete search history.

(56) References Cited

U.S. PATENT DOCUMENTS 4,305,296 A * 12/1981 Green et al. ............... 73/626
5,117,697 A *  6/1992 Takishita et al. .......... 73/626
(Continued)

FOREIGN PATENT DOCUMENTS

JP    2005192867        7/2005
WO   2007099473 A1   10/2000
(Continued)

*Primary Examiner* — Rajeev P Siripurapu

(57) ABSTRACT

A microbeamformer integrated circuit has sixty-lour microbeaauCormer channels which may be utilized with a 64-element or 128-element array transducer. Each microbeamformer channel includes a transmitter, a plurality of connection points for selectively coupling the transmitter to one or more transducer elements, a transmit/receive switch coupled to an output of the transmitter, and a receive channel including a variable delay. The connection points may be configured with only one connection point coupled to a transducer element, two connection points coupled to the same transducer element, or multiple connection points coupled to multiple transducer elements. The transmitter may also comprise a separate pulser coupled to each connection point. The receive channels are grouped in groups of sixteen which may be selectively coupled to one of two channel drivers to provide partially beamformed signals to the channels of a system beamformer.

13 Claims, 10 Drawing Sheets

(51) Int. Cl.
  *G01S 7/52* (2006.01)
  *G10K 11/34* (2006.01)

(52) U.S. Cl.
  CPC ........ *G01S 7/52017* (2013.01); *G10K 11/345* (2013.01); *G01S 15/8997* (2013.01)

(56) References Cited

U.S. PATENT DOCUMENTS

| | | | |
|---|---|---|---|
| 5,229,933 A | | 7/1993 | Larson, III |
| 5,520,187 A | | 5/1996 | Snyder |
| 5,573,001 A | * | 11/1996 | Petrofsky et al. ............ 600/447 |
| 5,902,241 A | | 5/1999 | Seyed-Bolorforosh et al. |
| 5,997,479 A | | 12/1999 | Savord |
| 6,013,032 A | | 1/2000 | Savord |
| 6,089,096 A | | 7/2000 | Alexandru |
| 6,102,863 A | | 8/2000 | Pflugrath |
| 6,126,602 A | * | 10/2000 | Savord et al. ................ 600/447 |
| 6,494,838 B2 | * | 12/2002 | Cooley et al. ................ 600/443 |
| 6,705,995 B1 | | 3/2004 | Poland |
| 6,995,730 B2 | * | 2/2006 | Pleva et al. .................... 343/876 |
| 7,439,656 B2 | | 10/2008 | Ossmann |
| 2003/0097071 A1 | | 5/2003 | Halmann |
| 2004/0181154 A1 | * | 9/2004 | Peterson et al. ............. 600/459 |
| 2005/0148874 A1 | * | 7/2005 | Brock-Fisher et al. ...... 600/447 |
| 2005/0203402 A1 | | 9/2005 | Angelsen |
| 2006/0241490 A1 | * | 10/2006 | Lazenby ....................... 600/472 |
| 2006/0264747 A1 | * | 11/2006 | Freeman et al. ............. 600/437 |
| 2008/0009741 A1 | * | 1/2008 | Hyuga .......................... 600/459 |
| 2009/0005684 A1 | * | 1/2009 | Kristoffersen et al. ....... 600/447 |

FOREIGN PATENT DOCUMENTS

| | | | |
|---|---|---|---|
| WO | WO 2005019856 A1 | * | 3/2005 |
| WO | WO 2006035384 A1 | * | 4/2006 |
| WO | WO2006/111873 | * | 10/2006 |
| WO | WO 2006111873 A2 | * | 10/2006 |
| WO | WO 2007099474 A1 | * | 9/2007 |

* cited by examiner

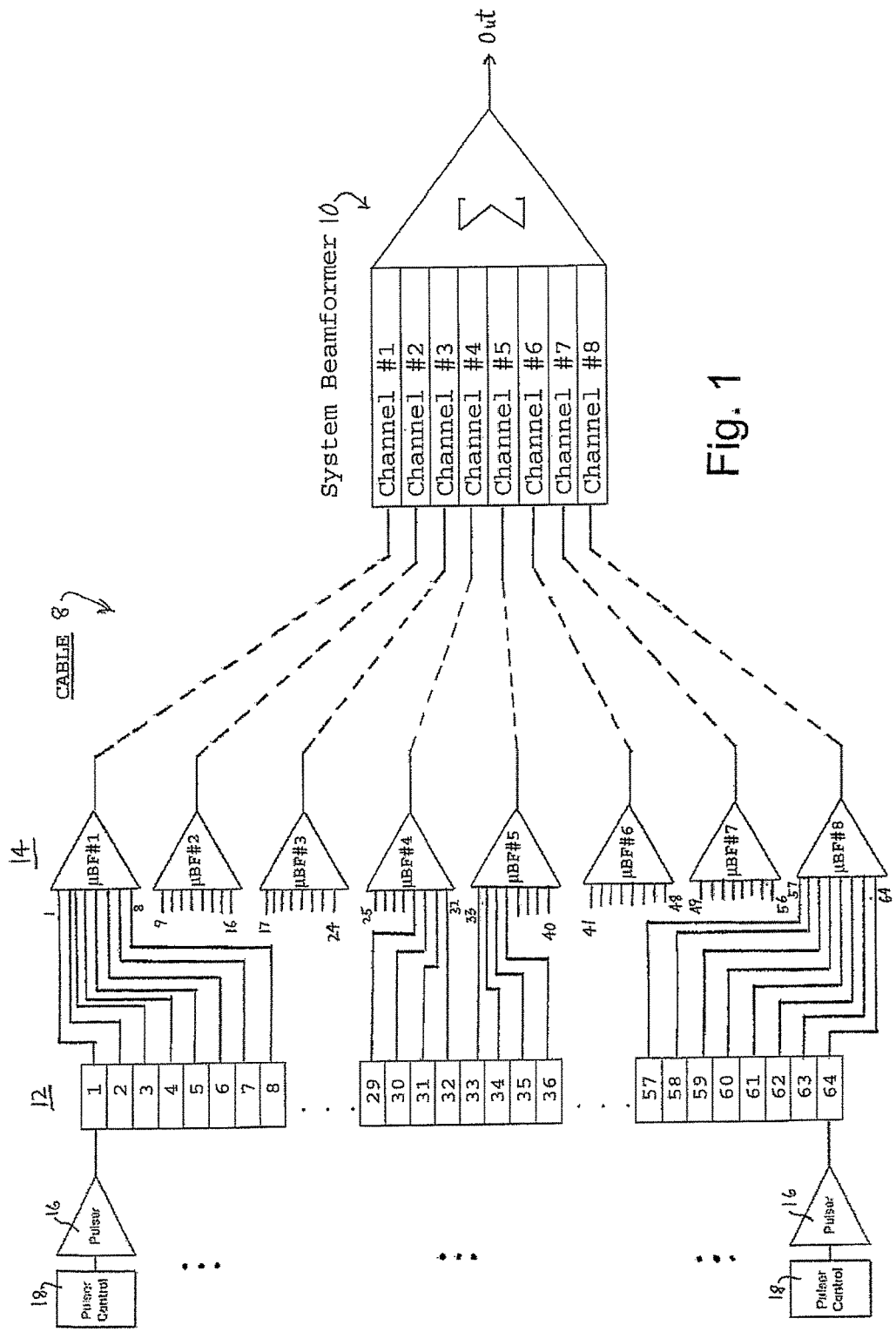

CONFIGURABLE MICROBEAMFORMER CIRCUIT FOR AN ULTRASONIC DIAGNOSTIC IMAGING SYSTEM

This invention relates to medical diagnostic ultrasound systems and, in particular, to a configurable microbeamformer circuit which can be used with different transducer arrays.

The term "microbeamformer" in ultrasonic imaging refers to delay and sum circuitry included in an ultrasonic probe to perform at least some of the beamforming for the array transducer in the probe. Because probes are handheld and need to be small and light so as to be convenient and comfortable for use by a sonographer, microbeamformers are generally implemented in integrated circuit form. See, for example, U.S. Pat. No. 7,439,656 (Ossmann). While originally designed for 3D imaging with two-dimensional transducer arrays as illustrated by U.S. Pat. No. 5,997,479 (Savord et al.), microbeamformers can also be used with one-dimensional transducer arrays used for 2D imaging. See U.S. Pat. No. 6,705,995 (Poland et al.) The microbeamformer can be used to perform all of the beamforming in the probe as illustrated by U.S. Pat. No. 6,102,863 (Pflugrath et al.), or can be used to perform only an initial portion of the beamforming with the balance of the beamforming performed in the system mainframe as illustrated by U.S. Pat. No. 5,229,933 (Larson, I I I) and the Savord et al. patent.

Integrated circuit chips which perform beamforming are no longer entirely custom designs, but are becoming standardized. For instance, eight channel beamformer chips are now being offered as standard parts. A drawback to such ICs is that they only can delay and sum eight channels in a chip, meaning that many ICs are necessary to beamform the signals from a typical 64-element, 128-element or greater 1D transducer array, and the outputs of the beamformer chips must still be combined to form the fully beamformed signal. An eight channel beamformer chip can be used to perform the final beamformation if the prior circuitry performs partial beamformation of no more than eight partially beamformed sums, however. But this presents the challenge of processing all of the signals from all of the elements down to eight partially beamformed sums, and doing so in an efficient and economical way that accommodates arrays of different numbers of transducer elements.

In accordance with the principles of the present invention, a beamformer circuit for an ultrasound probe is provided which is configurable to perform both transmit and receive beamforming for arrays of different sizes such as 64-element and 128-element transducer arrays. In one example described below the transmitters and receivers of the probe beamformer can be alternately connected to different transducer elements. This makes it possible to transmit and receive with the full aperture of a 64-element array and with half the aperture of a 128-element array with aperture translation and apodization control. In another example the beamformer circuit is able to transmit with the full aperture of either a 64-element or a 128-element array, with full aperture reception from a 64-element array and translatable half-aperture reception from a 128 element array. In a third example the microbeamformed receive channels are controllably coupled to different channel drivers for operation with a final beamformer with low channel count such as an eight-channel beamformer IC.

In the drawings:

FIG. 1 illustrates in block diagram form a beamformer for a 64-channel array transducer which provides partially beamformed sums for an eight-channel final beamformer.

Figure 5:
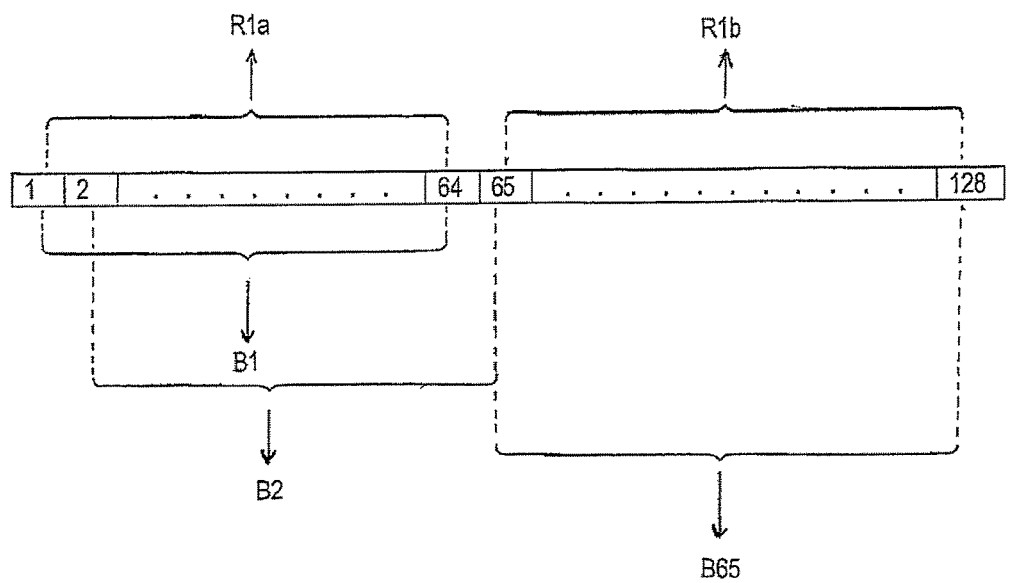
FIG. 5 illustrates transmit aperture translation and synthetic aperture reception using multiple transmitter and preamplifier combinations of FIG. 2.

Referring first to FIG. 1, a microbeamformer arrangement for a 64-element transducer array is shown in block diagram form. A 64-element transducer array 12 is represented by blocks which represent each of elements 1-8, 29-36 and 57-67 of the transducer array 12. For transmission each element is driven by a pulser 16 which drives its element with the desired pulse or waveform properly timed for that element. The timing of each pulser is controlled by a pulser control 18. In this example there are sixty-four pulsers, one driving each of the sixty-four transducer elements. This arrangement allows full use of the entire 64-element aperture for ultrasound transmission. The echo signals received by the transducer elements of the array 12 are coupled to eight microbeamformers 14, each microbeamformer having eight channels to process the signals received from eight transducer elements. Each microbeamformer channels amplifies and appropriately delays the echo signals received from its transducer element, then the eight amplified and delayed signals from the eight channels are combined to form a partially beamformed signal from eight transducer elements. The eight partially beamformed signals from the microbeamformers 14 are coupled to the inputs of eight channels of a system beamformer 10. Each channel of the system beamformer applies a common (bulk) delay to a partially beamformed signal and the eight channel signals are then combined to form a fully beamformed output signal. The microbeamformers and system beamformer can be partitioned in different ways. When the system beamformer is in the ultrasound system mainframe and the microbeamformer are in the probe as is the case in the aforementioned Savord et al. and Larson III patent, a probe cable 8 couples the microbeamformed signals to the system beamformer in the system mainframe. When all of the beamformation is performed in the probe as shown in the aforementioned Pflugrath et al. patent, the cable 8 will be printed circuit board traces or other conductors in the probe, as the system beamformer is then located in the probe. For a portable or handheld ultrasound system, the latter implementation is generally preferred.

The arrangement of FIG. 1 provides a separate transmitter and microbeamformer channel for each element of the transducer array 12. Thus, there is no compromise in performance as all of the elements can be simultaneously operated in parallel during both transmission and reception. One object of the present invention, though, is to provide a microbeamformer configuration which, with acceptable tradeoffs under the circumstances, can be used with different transducer arrays.

Figure 2:
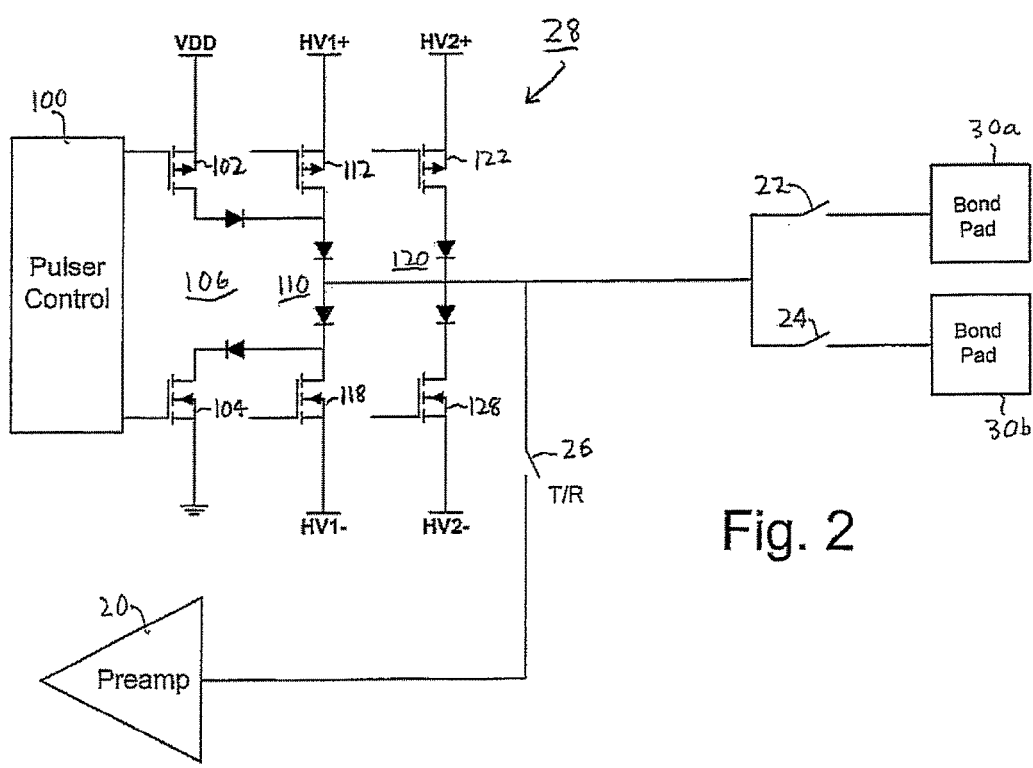
FIG. 2 illustrates in partial schematic and block diagram form a first transmitter and preamplifier combination which is switchable between two transducer elements.

Referring to FIG. 2, a transmitter and preamplifier portion of a microbeamformer channel constructed in accordance with the principles of the present invention is shown in schematic and block diagram form. In this example the transmitter is a dual level pulser as more fully described in concurrently filed U.S. provisional patent application Ser. No. 61/113,254 (Betts), entitled "DUAL PULSER FOR AN ULTRASONIC TRANSMITTER" and filed Nov. 11, 2008 the contents of which are incorporated herein by reference. The dual level pulser 28 includes one output stage 110 including transistors 112 and 118 which produce an output pulse at one of the bipolar high voltage supply levels HV1+ or HV1−. A second output stage 120 includes transistors 122 and 128 which produce an output pulse at one of the bipolar high voltage supply levels HV2+ or HV2−. Pulser control 100 selects one of the output stages and controls the pulse polarity produced. An active pull-to-ground stage 106, including transistors 102 and 104, pulls the output to ground level or other reference potential when a high voltage pulse is not being produced. The two output levels enable different level transmit waveforms to be produced and transmit apodization for sidelobe control. The two output stages of the pulser are both coupled to switches 22 and 24 which, in an IC implementation, are implemented as semiconductor switches. The switches are coupled to connection points for one or more transducer elements, shown in this example as bond pads 30a and 30b. In an integrated circuit embodiment of the present invention, the bond pads are electrical contacts on the exterior of the integrated circuit package where the circuitry of the IC can be bonded or electrically connected to an external circuit or device such as an element of an array transducer. If the transducer is fabricated in semiconductor form such as a CMUT or PMUT array, the transducer array and microbeamformer may be fabricated on a common IC, in which case the connection points would be internal to the IC. The junction of the two switches is coupled by a transmit/receive (T/R) switch 26 to the input of a preamplifier 20 of a microbeamformer receive channel. During transmission of a pulse the T/R switch is open to protect the preamplifier from the high voltage transmit signal, and after transmission when echoes are being received the T/R switch is closed to couple the echo signals to the microbeamformer channel for receive signal beamforming. The echo signals amplified by the preamplifier 20 are delayed then summed with other delayed echo signals from other transducer elements for beamformation.

Figure 3:
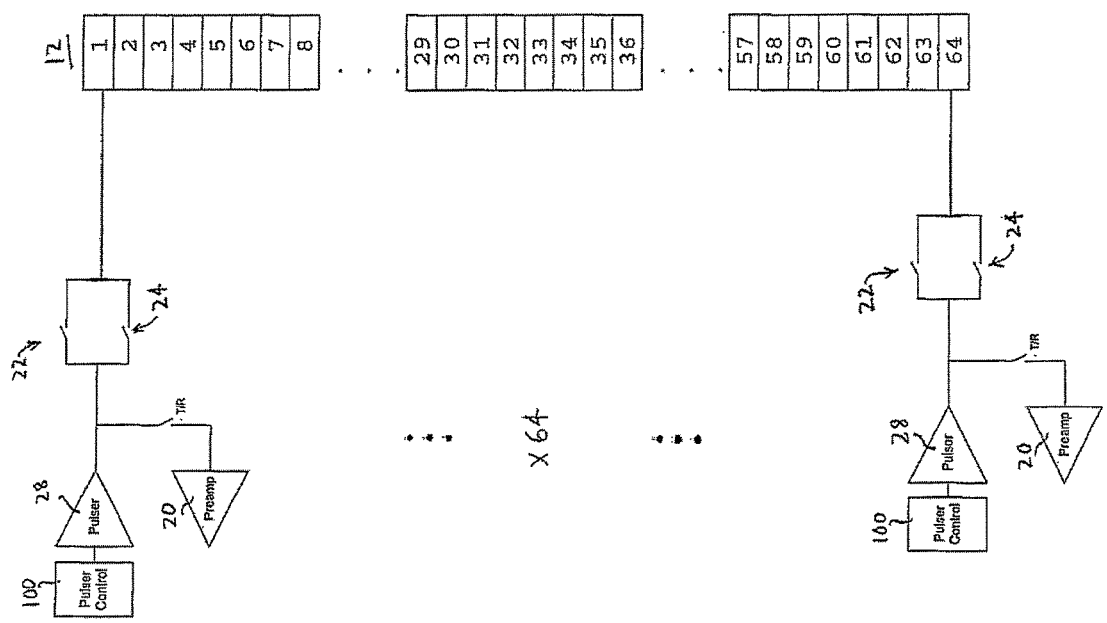
FIG. 3 illustrates the use of multiple transmitter and preamplifier combinations of FIG. 2 to perform transmission and reception with a 64-element transducer array.

FIG. 3 illustrates a first example of a 64-element transducer array 12 being operated by sixty-four of the combinations of FIG. 2 and the other associated components of each microbeamformer channel. In this implementation both switches 22 and 24 are coupled to the same transducer element or, alternatively, only one switch is coupled to the transducer element and the other switch is unused. It is not necessary to open or close the switches 22,24 in this implementation; they are closed at all times. The 64-element array is thus operated by sixty-four microbeamformer channels as exemplified by the channel sections coupled to elements 1 and 64. These sixty-four microbeamformer channels can be implemented on a single IC. During transmission all or some subset of the sixty-four transducer elements are driven by the sixty-four pulsers 28 of the microbeamformer channels. During echo reception the sixty-four T/R switches are closed and the echo signals received by the full array are amplified by the sixty-four preamplifiers 20, then forwarded to the rest of the microbeamformer channel for delaying and subsequent summation. The 64-element array can thereby be operated as a phased array or as a stepped linear array where the active aperture is stepped along the array from line to line.

Figure 4:
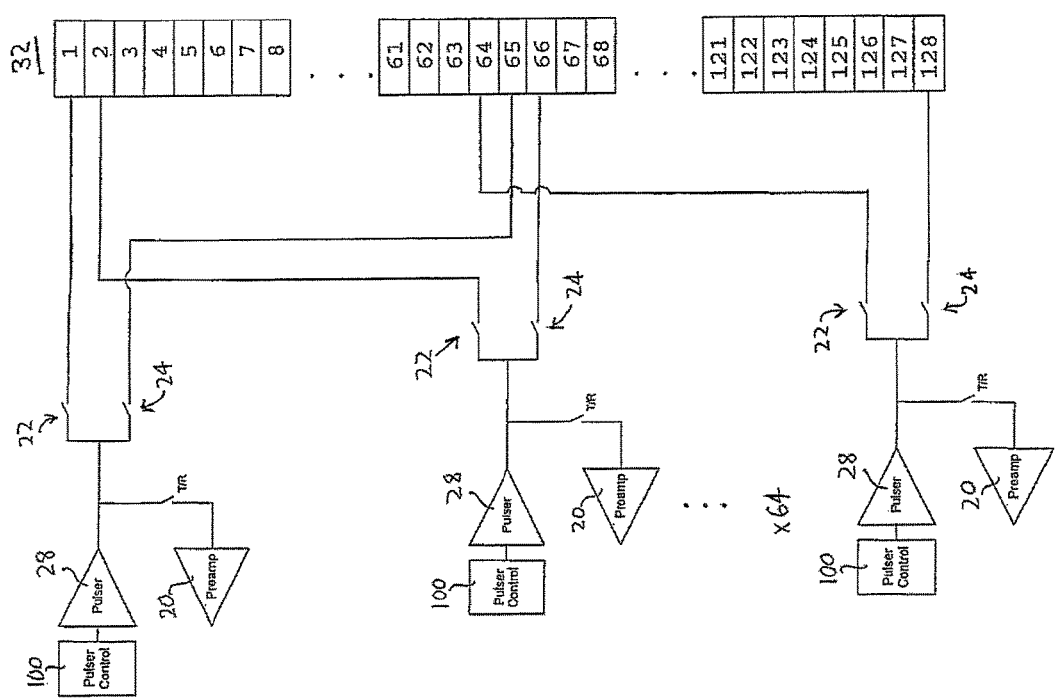
FIG. 4 illustrates the use of multiple transmitter and preamplifier combinations of FIG. 2 to perform transmission and reception with a 128-element transducer array.

FIG. 4 illustrates an example of use of the sixty-four microbeamformer channels of FIGS. 2 and 3 with a 128-element array transducer 32. In this embodiment the switches 22 and 24 are coupled to different transducer elements. A tradeoff is made in that a full 128-element aperture cannot be used during the same transmit-receive cycle. However, the switches 22,24 permit the aperture to be stepped along the transducer array so that the full aperture can be utilized in step-wise fashion. For example, when all of the switches 22 are closed, elements 1-64 are used for transmission. This is illustrated in FIG. 5 by the transmission of beam B1. The aperture is then stepped one element along the array by opening the switch 22 connected to element #1 and closing switch 24 on the same microbeamformer channel to couple the pulser of that microbeamformer channel to element #65 for transmission. By this switch change the transmit aperture now includes elements 2-65 to produce beam B2 as shown in FIG. 5. The transmit beams may be stepped in this manner until the last 64-element transmit aperture is reached to transmit beam B65 using elements 65-128 as shown in FIG. 5. Additional beams can be transmitted to the left of beam B1 and/or the right of beam B65 by using smaller transmit apertures to the left and right of those beams.

In this example the receive aperture steps with the transmit aperture, as each preamplifier 20 is coupled to the junction of switches 22 and 24. If the full 128-element aperture were desired for reception, the T/R switch is coupled to the output (junction of the switch and transducer element) of one of the switches 22,24, and a second T/R switch, preamplifier 20 and associated receive delay is coupled to the output of the other switch. This would make a full 128-element receive aperture available during each transmission by the 64-element transmit aperture.

However, the additional receive components are not necessary for a synthetic aperture implementation. In synthetic aperture imaging, the same transmit beam is transmitted twice. Following the first transmission, reception is done on half of the receive aperture, and following the second transmission reception is done on the other half of the receive aperture. The signals from both halves of the aperture, received in the two transmit-receive cycles, are then beamformed to produce a full aperture receive beam. This is also illustrated in FIG. 5. During a first transmission of beam B1 using elements 1-64, echo signals are received from elements 1-64 and saved or partially beamformed and saved as receive beam R1a. Beam B1 is transmitted a second time, but for reception the switches 22 used for transmission are opened and the switches 24 are closed so that echo signal are received from elements 65-128 and again saved or partially beamformed and saved as receive beam R1b, or beamformed together with the stored echo signals from the first beam transmission. Partial beams R1a and R1b are combined to form a full aperture receive signal. Thus, a full 128-element receive aperture can be used with the 64-element transmit aperture by the use of synthetic aperture beamformation using the same microbeamformer channel architecture as was used in FIG. 3.

Figure 6:
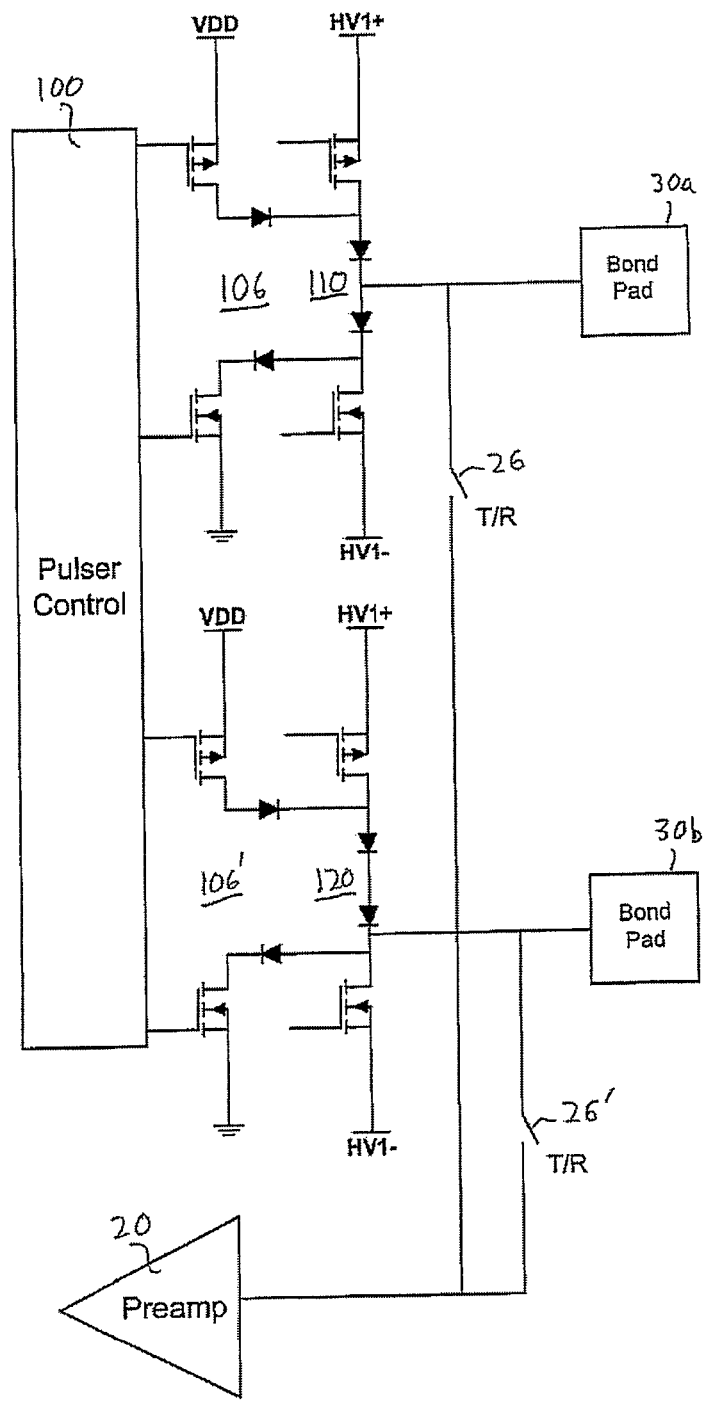
FIG. 6 illustrates in partial schematic and block diagram form a second transmitter and preamplifier combination which is switchable between two transducer elements.

FIG. 6 is a partial schematic and block diagram illustration of a second example of a microbeamformer channel transmitter and preamplifier of the present invention. In this embodiment the high voltage output stages 110 and 120 are separated and a second pull-to-ground stage 106' is added so that each separate output stage has its own pull-to-ground circuit. Each output stage is powered by the same bipolar high voltage supply HV1+, HV1−, although different supplies could be used if desired. The output of stage 110 can be connected to a transducer element #m, and the output of the other stage 120 can be connected to a different transducer element #n. Each transducer element connection is coupled by a T/R switch 26,26' to the preamplifier 20 for receive signal processing. This implementation provides the capability of driving a full 128-element transmit aperture with a pulser that utilizes substantially the same amount of IC area as the dual level pulser of FIG. 2. Furthermore, the signal path resistance and IC real estate utilized by the switches 22,24 have been eliminated.

An alternative use of the circuit in FIG. 6 can be obtained if the two pulsers 110 and 120 use different power supplies, resulting in a dual-level pulser similar to that described with respect to FIG. 2. In this case, the two bond pads 30a and 30b are connected to a single array element. The dual-level pulsar is used to provide transmit aperture apodization for sidelobe control. Thus the same circuit can be used to provide for either aperture translation or apodization, depending on the requirements of the specific application.

Figure 7:
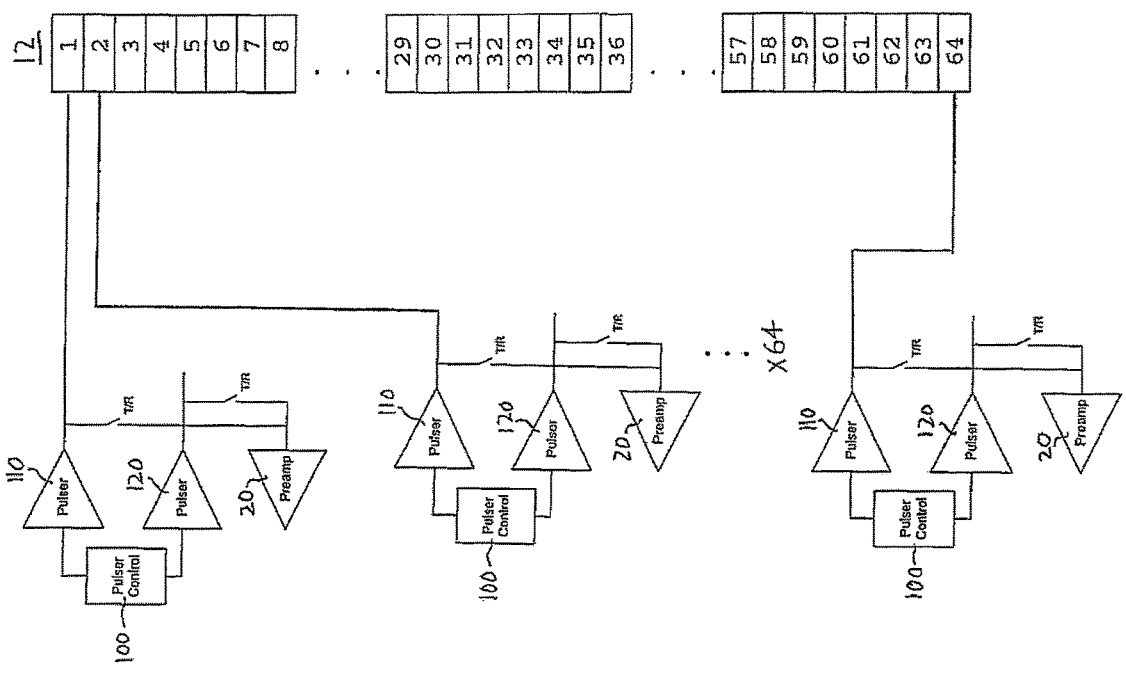
FIG. 7 illustrates the use of multiple transmitter and preamplifier combinations of FIG. 6 to perform transmission and reception with a 64-element transducer array.

FIG. 7 illustrates the use of the microbeamformer channel configuration of FIG. 6 with a 64-element transducer array 12. In this implementation there are sixty-four microbeamformer channels, each having two pulsers 110,120. Only half of these pulsers are needed to drive a 64-element array and FIG. 7 illustrates all of the pulsers 110 coupled to drive elements of the array 12. The pulsers 120 are unused in this implementation. Following transmission the T/R switch between the connected transducer element and the input of the respective preamplifier 20 is closed in all channels and the received echo signals of the sixty-four transducer elements are coupled to the sixty-four preamplifiers for amplification and subsequent receive beamforming.

Figure 8:
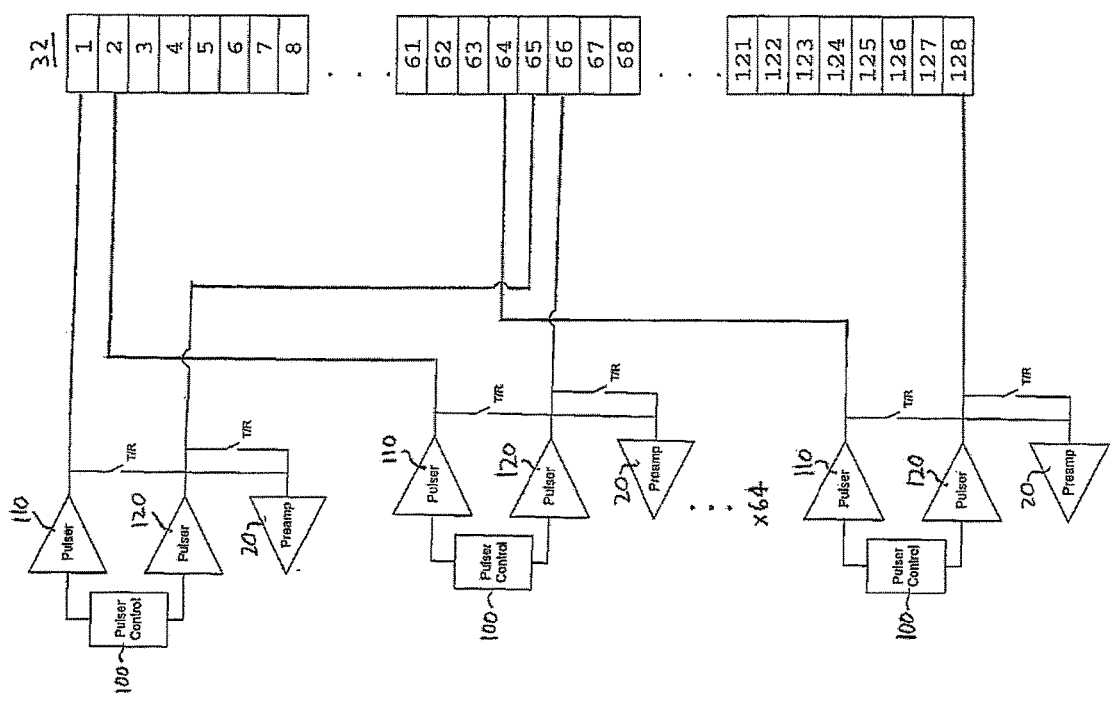
FIG. 8 illustrates the use of multiple transmitter and preamplifier combinations of FIG. 6 to perform transmission and reception with a 128-element transducer array.

In FIG. 8 the same sixty-four channel microbeamformer is used with a 128-element transducer array 32. The pulsers 110 are coupled to drive elements 1-64 of the array and the pulsers 120 are coupled to drive elements 65-128 of the array 32. This enables use of a full 128-element aperture for transmission. On receive one of the T/R switches in each channel is closed to direct the received echo signals from one of the transducer elements of the channel to the preamplifier 20 of the channel. This operation is similar to that of FIG. 4, where up to sixty-four elements can be coupled for reception at the same time, and synthetic aperture receive beamforming is possible by successively receiving on alternate halves of the full 128-element aperture.

Figure 9:
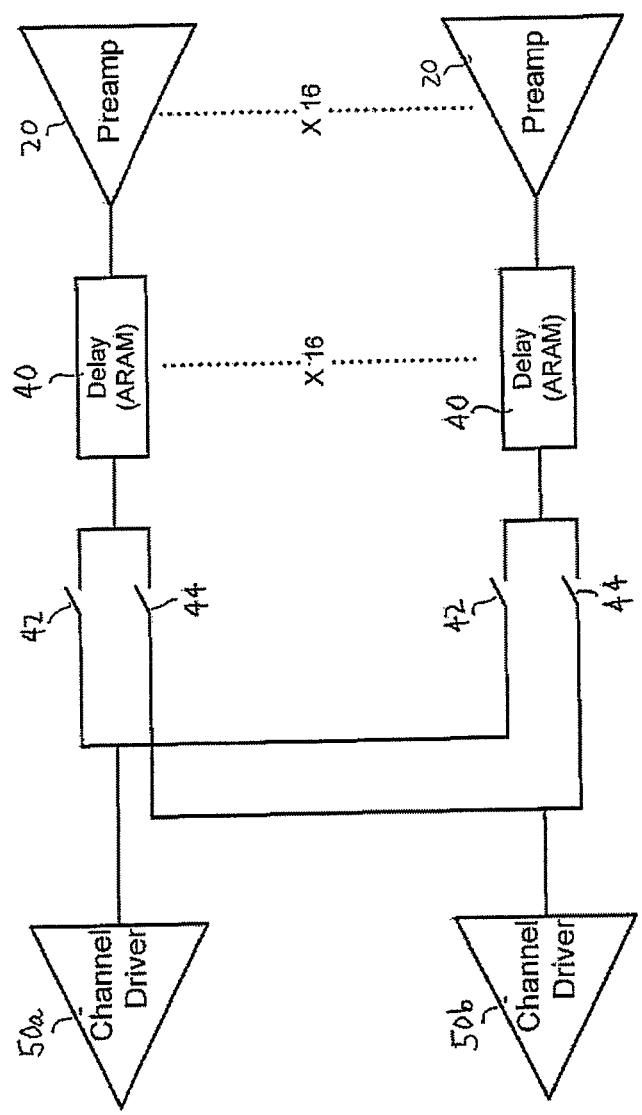
FIG. 9 illustrates in block diagram form a plurality of microbeamformer receive channels which may be selectively coupled to two channel drivers.

FIG. 9 illustrates an arrangement of components of microbeamformer receive channels by which a microbeamformer can be used with 64-element or 128-element arrays for full aperture beamforming. In this example each microbeamformer receive channel includes a preamplifier 20 coupled to a delay 40. In this example the delay is provided by an analog random access memory (ARAM) delay as described in the above-mentioned Poland et al. and Savord et al. patents. The delayed echo signals produced by the delay 40 are then steered by switches 42 or 44 to the input of one of two channel drivers 50a or 50b. The channel drivers function to couple one or more microbeamformer channel receive signals to a subsequent processor such as a channel of a system beamformer. In a given implementation the channel driver can be complex and provide functions such as summation and amplification, or it can be as simple as a conductor which couples signals to a subsequent channel and may also function as a summing node. When multiple echo signals are coupled to the input of a channel driver at the same time they are effectively summed at that junction. The combined echo signals at the input of a channel driver are coupled by the channel driver for subsequent processing, such as the completion of beamforming if the echo signals are a partially beamformed signal. The arrangement of FIG. 9 is seen to comprise sixteen microbeamformer channels which may be selectively coupled to the two channel drivers 50a and 50b. When all sixteen switches 42 are closed, all sixteen receive channels are coupled to channel driver 50a, and when all sixteen switches 44 are closed, all of the channels are coupled to channel driver 50b. Other combinations of switch closures will apportion the channels among the two channel drivers accordingly.

Figure 10:
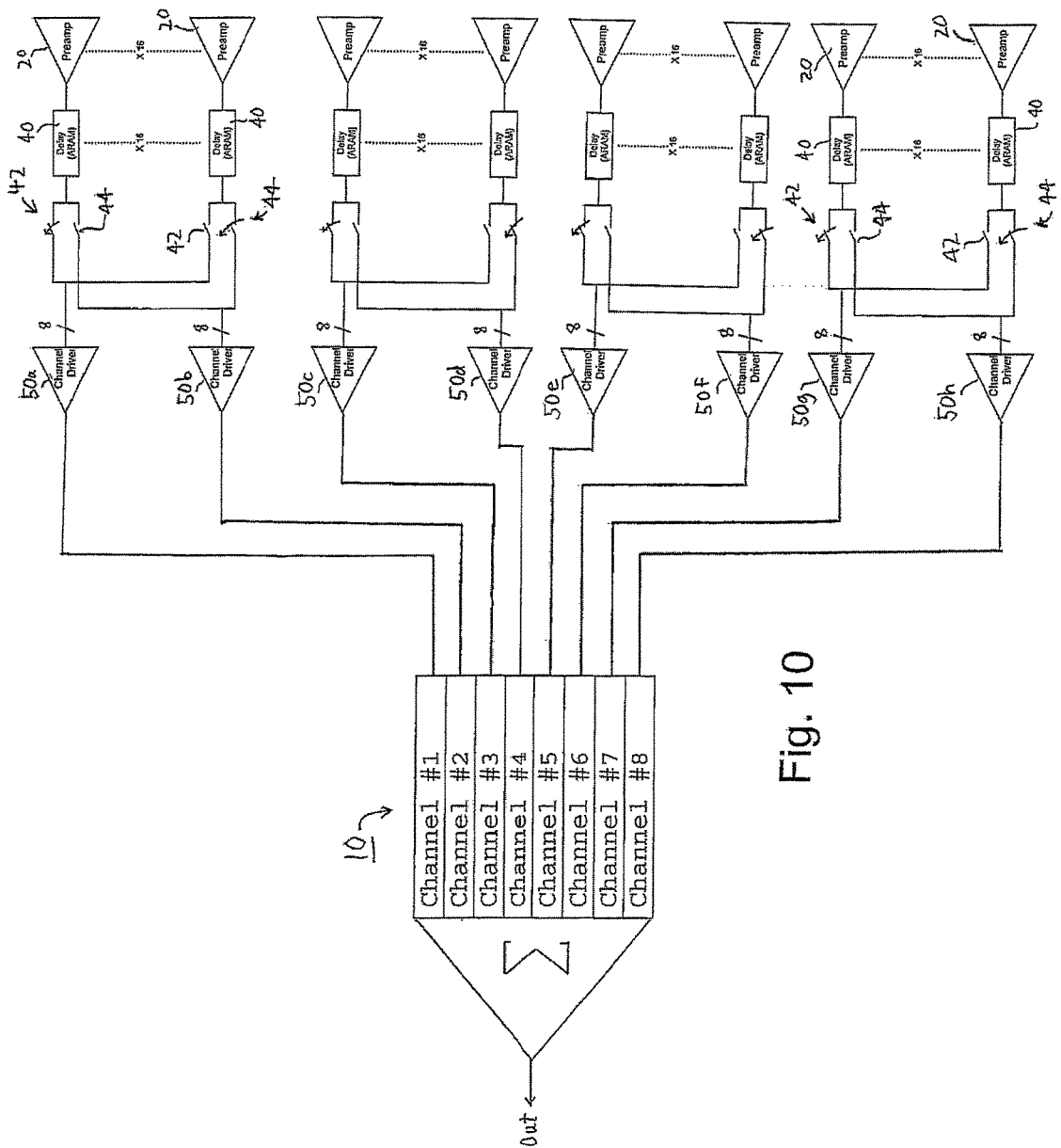
FIG. 10 illustrates the use of the microbeamformer receive channels and channel drivers of FIG. 9 to couple a 64-element transducer array to an eight-channel beamformer.

FIG. 10 is an example of the use of a microbeamformer with four of the arrangements of FIG. 9 with an eight-channel system beamformer 10. The four receive channel arrangements each have two channel drivers and thus a total of eight channel drivers, identified by 50a-50h in FIG. 10, are provided. In each group, eight of switches 42 are closed to couple the delayed echo signals of eight microbeamformer channels to one of the two channel drivers and eight of switches 44 are closed to couple echo signals from the other eight microbeamformer channels to the input of the other channel driver. For instance, in the upper channel grouping of FIG. 10, the top eight receive channels are coupled to the input of channel driver 50a, and the lower eight receive channels are coupled to the input of channel driver 50b. With the switches of each group of sixteen channels set in this manner, it is seen that eight microbeamformer channels from eight elements of a 64-element array are coupled to the input of each channel driver 50a-50h, which evenly distributes the echo signals from the sixty-four elements to the eight channel drivers. The output of each channel driver is coupled to a different channel of the eight-channel system beamformer 10, which combines the partially beamformed signals of the channel drivers into a fully beamformed signal at the output of the system beamformer 10.

Figure 11:
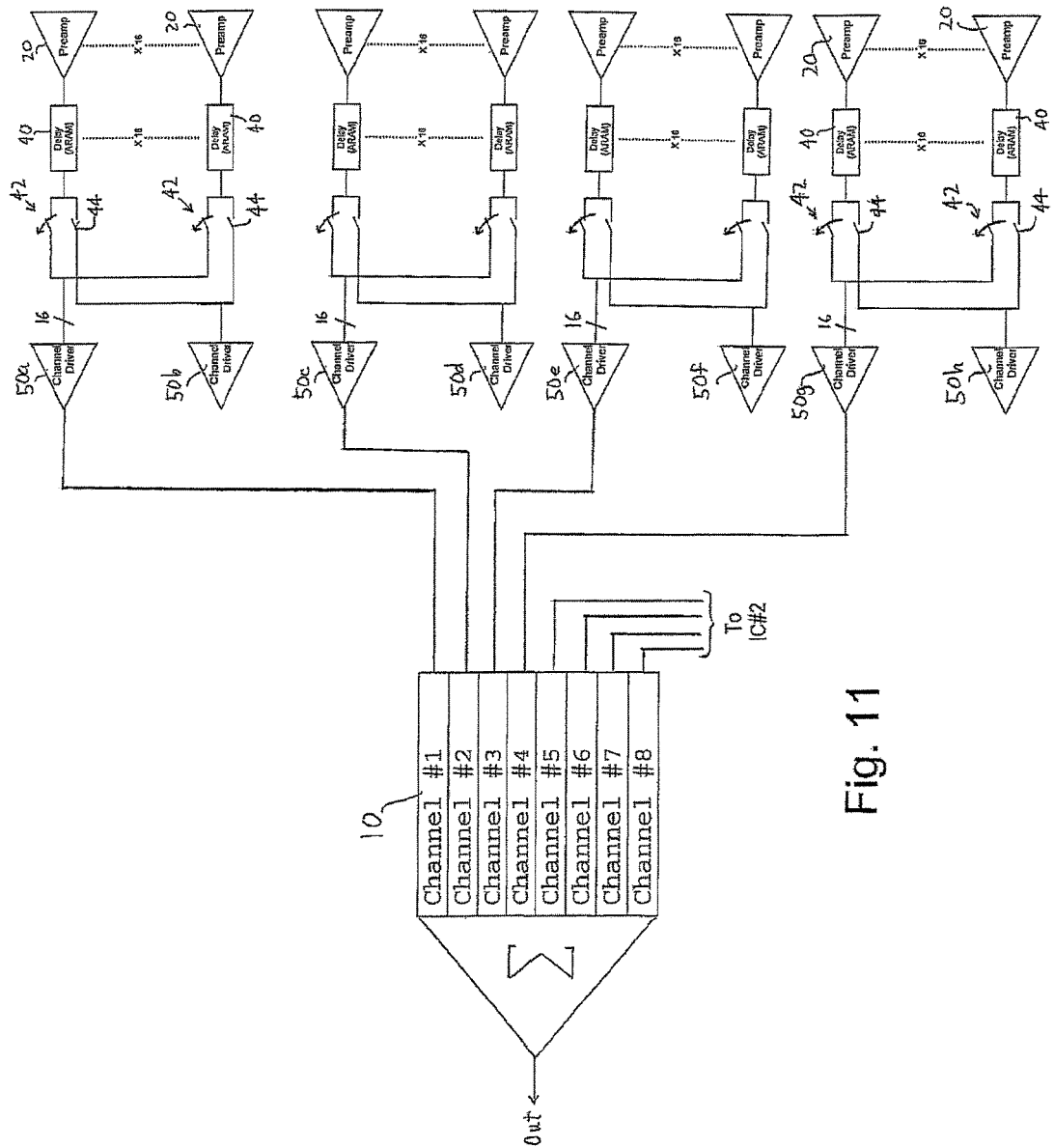
FIG. 11 illustrates the use of the microbeamformer receive channels and channel drivers of FIG. 9 to couple a 128-element transducer array to an eight-channel beamformer.

In the example of FIG. 11 the receive microbeamformer channel arrangement of FIG. 9 is used with a 128-element transducer array. For purposes of this example it is assumed that the four microbeamformer channel grouping shown on the right side of FIG. 10 are integrated onto one IC. That IC is used to provide the microbeamformer channel grouping shown on the right side of FIG. 11. As before, this microbeamformer channel grouping receives and processes echo signals from sixty-four transducer elements, in this example comprising elements 1-64 of a 128-element array transducer. In the use with a 128-element array, all of switches 42 in each grouping are closed and all of switches 44 are left open as shown in the drawing. This switch setting applies all sixteen echo signals from the sixteen elements coupled to the sixteen preamplifiers 20 to a single channel driver. In the upper grouping of sixteen microbeamformer channels in FIG. 11, the echo signals from elements 1-16 of the 128-element array are all applied to the input of channel driver

50*a*. Channel driver 50*b* plays no role in this implementation. With all of the switches 42 closed as shown, it is seen that each of channel drivers 50*a*, 50*c*, 50*e*, and 50*g* provide a partially beamformed sum of sixteen microbeamformer channels to one of channels 1-4 of the system beamformer 10.

FIG. 11 as described to this point shows how the echo signals of sixty-four elements of the 128-element array, elements 1-64 in this example, are handled by an IC including the receive channel groupings shown on the right side of FIG. 11. To handle the remaining sixty-four elements, a second IC like this one is configured to receive echo signals from the remaining sixty-four elements in a similar manner. As FIG. 11 shows, the signals for channels 5-8 of the system beamformer are provided by this second IC, which is coupled to process the echo signals from transducer elements 65-128 in the same manner as the sixty-four microbeamformer channels shown in detail in FIG. 11.

It is seen that various combinations of the microbeamformer transmitters and receive channel arrangements described above may be combined and integrated into an IC which can be used with different size transducer arrays, in particular, with either a 64-element array or a 128-element array. It is thus necessary to go to the expense of fabricating only one IC to serve the needs of both sizes of arrays. It will also be seen that variations will readily occur to those skilled in the art. For example, the parallel single pole, single throw switch pairs shown in FIGS. 2, 6, and 9 can each be fabricated as a single pole, double throw switch to accomplish the same purpose. Different or higher levels of integration may be desirable for different target sizes of transducer arrays and system beamformers.

It will be recognized that a microbeamformer IC implementation of the present invention can be scaled up or down to accommodate different channel counts and combinations. While a 64/128 channel combination is illustrated above, it is understood that other combinations such as 48/192 channels or 32/128 channels may also be implemented, as long as the higher channel count implementation is an integer multiple of the number of channels of a lower channel count IC.

What is claimed is:

1. An ultrasonic probe comprising:
a transducer array comprising one or more transducer elements; and a microbeamformer integrated circuit including a plurality of transmitter and receive channels selectively coupled to the transducer elements, at least one microbeamformer transmitter and receive channel of the plurality comprising:
a transmitter circuit having an output for delivering a transducer drive signal, and operable to deliver the drive signal in a controllably timed relationship with other transmitter circuits;
a plurality of connection points between the transmitter output and one or more transducer elements by which the transmitter output is selectively coupled to the one or more transducer elements to selectively couple the transducer drive signal to at least one selected transducer element;
a transmit/receive switch coupled to at least one of the connection points; and a receive channel coupled to the transmit/receive switch
wherein the transmitter circuit further comprises:
a first pulser having an output for delivering a first transducer drive signal, the first pulser output being coupled to a first connection point of the plurality of connection points; and a second pulser having an output for delivering a second transducer drive signal, the second pulser output being coupled to a second connection point of the plurality of connection points; and
wherein the transmit/receive switch further comprises:
a first transmit/receive switch coupled between the first connection point and the receive channel; and
a second transmit/receive switch coupled between the second connection point and the receive channel.

2. The ultrasonic probe of claim 1, wherein the connection points further comprise a first switch which may be closed to couple the transducer drive signal to a first connection point of the plurality, and a second switch which may be closed to couple the transducer drive signal to a second connection point of the plurality.

3. The ultrasonic probe of claim 1, wherein the plurality of connection points are coupled to only one transducer element of the transducer array.

4. The ultrasonic probe of claim 3, wherein the transducer array comprises sixty-four transducer elements and the microbeamformer integrated circuit comprises sixty-four microbeamformer transmitter and receive channels, each comprising a transmitter circuit, at least one connection point coupled to an output of the respective transmitter circuit, a transmit/receive switch, and a receive channel coupled to the transmit/receive switch, and
wherein the at least one connection point of each of the microbeamformer channels is coupled to a different transducer element of the sixty-four transducer elements.

5. The ultrasonic probe of claim 1, wherein the plurality of connection points comprises a first connection point and a second connection point, and the first and second connection points are coupled to different transducer elements.

6. The ultrasonic probe of claim 5, wherein the transducer array comprises 128 transducer elements and the microbeamformer integrated circuit comprises sixty-four microbeamformer transmitter and receive channels, each comprising a transmitter circuit, at least two connection points selectively coupled to an output of the respective transmitter circuit, a transmit/receive switch, and a receive channel coupled to the transmit/receive switch,
wherein the connection points of each of the microbeamformer channels are coupled to a different transducer element of the 128 transducer elements.

7. The ultrasonic probe of claim 1, wherein the transducer array comprises sixty-four transducer elements;
wherein the microbeamformer integrated circuit comprises sixty-four microbeamformer transmitter and receive channels, each comprising a plurality of transmitter circuits, at least one connection point coupled to an output of each transmitter circuit, a plurality of transmit/receive switches, and a receive channel coupled to the transmit/receive switches,
wherein the at least one connection point of each of the microbeamformer channels is coupled to a different transducer element of the sixty-four transducer elements.

8. The ultrasonic probe of claim 1, wherein the transducer array comprises 128 transducer elements and the microbeamformer integrated circuit comprises sixty-four microbeamformer transmitter and receive channels, each comprising a plurality of transmitter circuits, a connection point coupled to an output of each transmitter circuit, a plurality of transmit/receive switches, and a receive channel coupled to the transmit/receive switches, wherein the connection points of each of the microbeamformer transmitter and receive channels are coupled to a different transducer element of the 128 transducer elements.

9. The ultrasonic probe of claim 1, wherein the at least one transmitter and receive channel further comprises an amplifier having an output coupled to a channel delay and an input coupled to the transmit/receive switch; and further comprising:
a plurality of additional transmitter and receive channels, each comprising an amplifier having an input coupled to receive echo signals from a transducer element and an output coupled to a channel delay;
a plurality of channel drivers; and
a plurality of switches coupled between the channel delays of the transmitter and receive channels and the channel drivers for selectively applying delayed echo signals to a respective channel driver in the plurality.

10. The ultrasonic probe of claim 9, wherein the transducer array comprises a 64-element transducer array;
wherein the microbeamformer integrated circuit comprises sixty-four microbeamformer transmitter and receive channels, each comprising a transmitter circuit, at least one connection point coupled to an output of the transmitter circuit, a transmit/receive switch, and a receive channel coupled to the transmit/receive switch,
wherein the sixty-four channels are configured in groups of sixteen channels, the channels of each group may be selectively coupled to one of two channel drivers by a plurality of switches; and
wherein the channel drivers are coupled to inputs of channels of a system beamformer.

11. The ultrasonic probe of claim 10, wherein the plurality of switches are set to couple eight microbeamformer channels to each channel driver.

12. The ultrasonic probe of claim 9, wherein the transducer array comprises a 128-element transducer array;
wherein the microbeamformer integrated circuit comprises sixty-four microbeamformer transmitter and receive channels, each comprising a transmitter circuit, at least one connection point coupled to an output of a transmitter circuit, a transmit/receive switch, and a receive channel coupled to the transmit/receive switch,
wherein the sixty-four channels are configured in groups of sixteen channels, the channels of each group may be selectively coupled to one of two channel drivers by a plurality of switches; and
wherein the plurality of switches are set to couple the channels of each group to one channel driver; and
wherein the channel drivers coupled to microbeamformer channels by the switches are coupled to inputs of channels of a system beamformer.

13. The ultrasonic probe of claim 12, further comprising:
a second microbeamformer integrated circuit of sixty-four microbeamformer transmitter and receive channels, configured with switch settings the same as those of the microbeamformer integrated circuit,
wherein the channel drivers coupled to microbeamformer channels of the second microbeamformer integrated circuit by the switches of the second microbeamformer integrated circuit are coupled to inputs of channels of the system beamformer.

* * * * *